Figure 1:
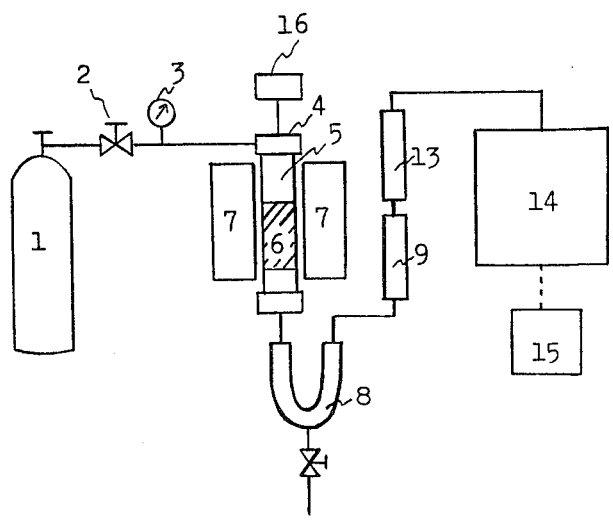

United States Patent [19]
Oi et al.

[11] 4,332,591
[45] Jun. 1, 1982

[54] ANALYTICAL METHOD AND APPARATUS FOR THE DETERMINATION OF TOTAL NITROGEN CONTENTS IN AQUEOUS SYSTEMS

[75] Inventors: Naobumi Oi, Kyoto; Tadamasa Itoh; Yoshiaki Yasumasa, both of Toyonaka, all of Japan

[73] Assignee: Sumitomo Chemical Company, Limited, Osaka, Japan

[21] Appl. No.: 974,540

[22] Filed: Dec. 29, 1978

[30] Foreign Application Priority Data

Jan. 19, 1978 [JP] Japan .................................. 53/5066
Jan. 31, 1978 [JP] Japan ................................. 53/10243

[51] Int. Cl.$^3$ .............................................. G01N 31/12
[52] U.S. Cl. .................................. 23/230 PC; 422/78; 422/80; 422/89
[58] Field of Search ............... 23/230 PC; 422/78, 80, 422/89, 98; 73/23.1, 26

[56] References Cited

U.S. PATENT DOCUMENTS 3,304,159  2/1967  Hinsvark ..................... 23/230 PC
4,015,936  4/1977  Kumazawa ................... 23/230 PC
4,025,309  5/1977  Hach ............................. 23/230 PC
4,066,402  1/1978  Komiyama et al. ............ 23/230 PC
4,095,949  6/1978  Flett ............................. 23/230 PC

OTHER PUBLICATIONS

Friedel et al.; Mass Spectrometric Analysis of Mixtures Containing Nitrogen Dioxide; Anal. Chem. vol. 25, No. 9, Sep. 1953, pp. 1314–1320.
Ryhage; Use of a Mass Spectrometer as a Detector and Analyzer for Effluents Emerging from High Temperature Gas Liquid Chem. Column; Analytical Chem., vol. 36, No. 4, Apr. 1964, pp. 759–764.

Primary Examiner—Michael S. Marcus
Attorney, Agent, or Firm—Birch, Stewart, Kolasch & Birch

[57] ABSTRACT

An analytical method for the determination of the total nitrogen content in aqueous systems, which comprises passing an inert gas stream containing substantially no nitrogen and carbon dioxide through a reaction tube, which is packed with a decomposition catalyst and maintained at a temperature of 700° to 1200° C., a condenser and a moisture-absorbing tube in this order, injecting an aqueous test sample to be analyzed into the reaction tube, and sending the gaseous products coming out of the moisture-absorbing tube to a mass spectrometer to determine the nitrogen content, and an apparatus for carrying out such a method. By this method, it is possible to determine the total nitrogen content in nitrogen compounds contained in aqueous systems, rapidly, accurately and with a high sensitivity.

4 Claims, 4 Drawing Figures

ANALYTICAL METHOD AND APPARATUS FOR THE DETERMINATION OF TOTAL NITROGEN CONTENTS IN AQUEOUS SYSTEMS

The present invention relates to a method for the determination of the total nitrogen content in aqueous systems such as sea water, river water, lake or marsh water and various waste waters, and an apparatus for carrying out such a method. In view of problems of environmental pollution in water areas, such as nutritional enrichment and red water formation, the development of an analytical method for the rapid and accurate determination of total nitrogen content is highly desired.

For analyzing the total nitrogen content in aqueous systems, there are known wet chemical methods such as the Kjeldahl method, which however require an extremely long time for measurement. Further, in order to obtain accurate analytical values, sufficient knowledge concerning the reactions applied to the analysis and on the influences of co-existing components and measurement conditions are necessary. Furthermore, persons who carry out the analytical methods are required to have high levels of knowledge and skill. As to instrumental analysis, various methods have been proposed, for example, the coulometric detection of ammonia produced from the hydrogenative decomposition of nitrogen compounds, detection by chemiluminescence which is emitted when nitrogen monoxide derived from nitrogen compounds is changed into nitrogen dioxide by reaction with ozone, detection of nitrogen monoxide derived from nitrogen compounds by means of a non-dispersion infrared analyzer, and detection of nitrogen gas produced from nitrogen compounds by means of a gas chromatograph with a thermal conductivity detector. In the coulometric detection, hydrogen gas is used for hydrogenative decomposition at high temperatures and hence a great care must be given to safety in operation. The methods using a non-dispersion infrared analyzer or a gas chromatograph with a thermal conductivity detector have drawbacks such as insufficient sensitivity or abnormality in the chromatogram owing to interfering substances, when the samples to be analyzed have a low nitrogen content. Under the circumstances, the present inventors have conducted intensive studies on an analytical method for the determination of total nitrogen content in aqueous systems without the drawbacks as in the known methods and have found an improved method and an apparatus therefor.

An object of the present invention is to provide a novel method for determining the total nitrogen content in nitrogen compounds contained in aqueous systems rapidly, accurately and with a high sensitivity. Another object of the present invention is to provide an apparatus for carrying out the method. Other objects and advantages of the present invention will become apparent from the following description.

The present invention provides a method for the determination of the total nitrogen content in aqueous systems, which comprises passing an inert gas stream containing substantially no nitrogen and carbon monoxide through a reaction tube, which is packed with a decomposition catalyst and maintained at a temperature of 700° to 1200° C., a condenser and a moisture-absorbing tube in this order, injecting an aqueous test sample to be analyzed into the reaction tube, and sending the gaseous products coming out of the moisture-absorbing tube to a mass spectrometer to determine the nitrogen content, and an apparatus for carrying out such a method.

According to the present invention, the total nitrogen content in aqueous systems can be determined stably and in a high-sensitivity by using a mass spectrometer because of a high sensitivity to nitrogen gas thereof and little interference owing to the interfering substances in the reaction system.

Examples of the inert gas used in the present invention are rare gases such as helium and argon. The reaction tube is made of a heat and corrosion resistant material such as quartz or ceramics. As the decomposition catalyst, the platinum group metals such as platinum and palladium are favorable in terms of a high stability to high temperatures. The catalyst may be employed in any form (e.g. pellets, wires, gauzes) which does not inhibit the flow of a gas. For example, the catalyst may be used in the form that the metal is deposited on a carrier such as alumina or asbestos. The catalyst is preferably maintained at a temperature of 700° to 1200° C. The catalyst participates in decomposition of nitrogen compounds with water into lower compounds and nitrogen at such a high temperature.

The condenser is provided in order to cool and condense water vapor generated in the high-temperature reaction zone (i.e. the reaction tube) and to properly discharge the condensed water out of the system through a cock attached thereto. The cooling is carried out by air, water, ice or an electronic cooler. The condenser functions not only for discharging water and salts out of the system but also is helpful for prolonging the lives of a moisture absorber in the subsequent moisture-absorbing tube, and an oxidizing agent and a reducing agent in the low-temperature reaction tube which is optionally provided as described hereinafter.

As the moisture-absorbing tube, a tube packed with a moisture absorber (e.g. magnesium perchlorate, calcium chloride, phosphorus pentoxide, an ion-exchange resin) is used.

In the present invention, as described above, it is desirable to provide a low-temperature reaction tube which is packed with an oxidizing agent or a reducing agent or both and maintained at a temperature of 300° to 700° C., after the moisture-absorbing tube. This low-temperature reaction tube is particularly effective when the samples to be analyzed have a high nitrogen content.

As the oxidizing agent, copper oxide or cobalt oxide having a high oxidizing power at the above-described temperature is preferred. The oxidizing agent may be used in any form of pellets, wires and gauzes. The oxidizing agent mainly acts to remove hydrogen from the gaseous products produced in the layer of decomposition catalyst.

As the reducing agent, reduced copper or reduced nickel is preferred in terms of a high reducing power and chemical stability thereof. The reducing agent may be employed in any form of pellets, wires and gauzes. The reducing agent mainly acts to remove oxygen from the gaseous products produced in the layer of decomposition catalyst.

It is desirable to maintain the oxidizing agent and reducing agent at a temperature of 300° to 700° C., and both agents may be packed in any order. Occasionally, either of them may be used alone according to the particular objectives involved. For example, when the aqueous sample to be analyzed contains organic substances in a low concentration, it is sufficient to use the reducing agent alone and on the other hand, when the concentration of nitrogen compounds in the aqueous sample is low, only the oxidizing agent may be used alone.

The gaseous products passed through the moisture-absorbing tube and/or the low-temperature reaction tube are introduced into a mass spectrometer, where it is desirable to provide a carbon dioxide-absorbing tube preceding the mass spectrometer. As the carbon dioxide-absorbing tube, a tube packed with a carbon dioxide absorber such as soda asbestos is used. When the moisture absorber packed in the moisture absorbing tube is a substance which can also absorb carbon dioxide gas, this carbon dioxide-absorbing tube can be omitted.

The mass spectrometer used for the detection of nitrogen is not specifically limited, but there can be used any type of mass spectrometer, which can be used for gas chromatography, such as a single focus type, double focus type and quadrupole type.

An ion source for the mass spectrometer is preferably of an electron impact type. The detection is carried out with a total ion monitor or by mass fragmentgraphy. According to the mass fragmentgraphy, the determination can usually be done with a higher sensitivity, because it is not influenced by other components in the reaction system.

One example of the analytical method and apparatus of the present invention will be illustrated specifically with reference to the accompanying drawing.

Figure 2:
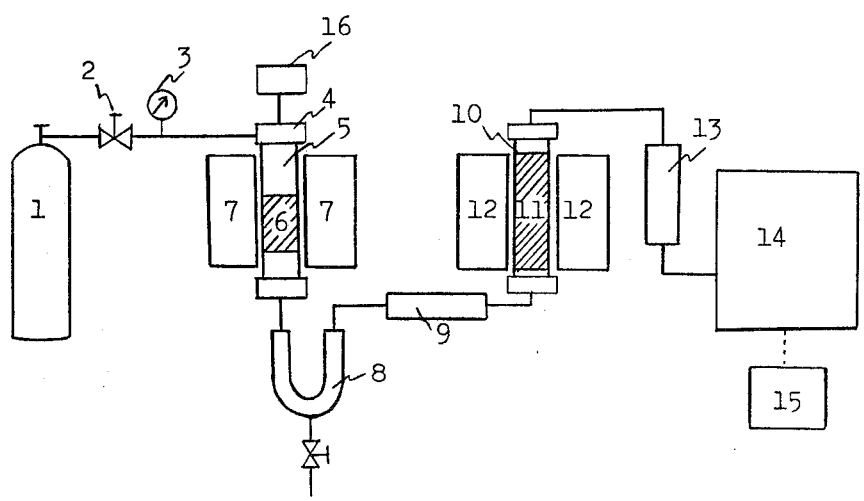
Figure 3:
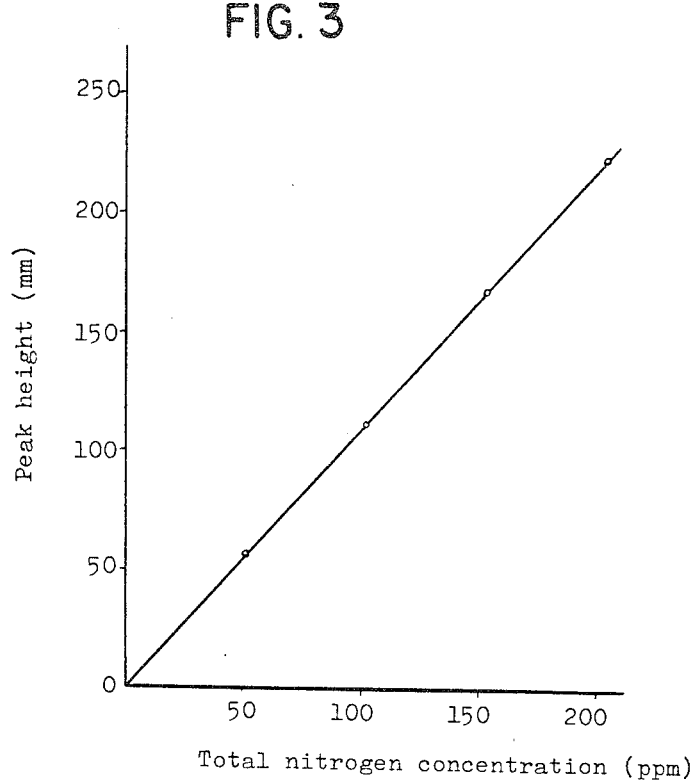
Figure 4:
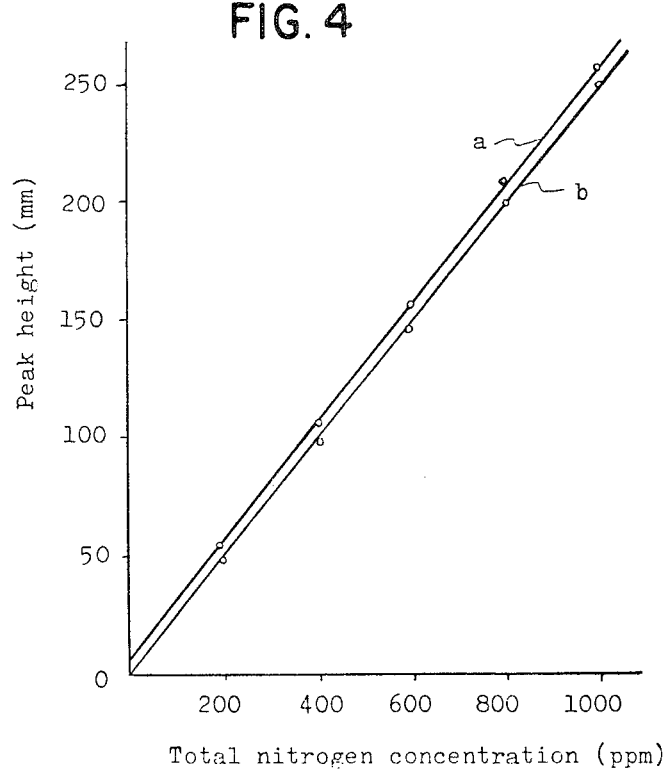

FIGS. 1 and 2 are a schematic diagram of the apparatus according to the present invention, and FIGS. 3 and 4 are the calibration curves of aqueous urea solutions obtained in Examples 1 and 2, respectively.

As is shown in FIG. 1 and FIG. 2, an inert gas from an inert gas source 1 such as a helium or argon bomb passes through a pressure controller 2 and a pressure gauge 3, and is led to the inlet 4 of a high-temperature reactor tube 5, at a constant flow rate. An inlet for test samples is attached to the inlet 4. The flow rate of the gas is determined depending upon the degree of vacuum of the mass spectrometer, but the flow rate is usually in the range of about 10 to 25 ml/minute. The reaction tube 5 is made of quartz or ceramics, and preferably it has an inner diameter of 7 to 15 mm and an inner volume of 7 to 50 ml. In the reaction tube 5, there is provided a decomposition catalyst layer 6 and the reaction tube is heated at about 700° to 1200° C. with an electric furnace 7.

An aqueous test sample to be analyzed is injected into the reaction tube 5 from the inlet 4 by means of, for example, a microsyringe or an automatic injector 16. In the reaction tube 5, the nitrogen compounds contained in the aqueous test sample are decomposed and gaseous products are produced. The gaseous products thus produced pass through a condenser 8 which is equipped with a draining cock, and a moisture-absorbing tube 9 which is packed with a moisture absorber, wherein the gaseous products are carried on the inert gas stream. By this treatment, the gaseous products are cooled and the condensed water and moisture are removed therefrom. The gaseous products thus treated are introduced into a mass spectrometer 14 optionally via a carbon dioxide-absorbing tube 13 which is packed with a carbon dioxide absorber. The signals obtained in the mass spectrometer are sent to a data processing zone 15 through a signal line. Data processing is carried out with a recorder, digital integrator and the like.

As is shown in FIG. 2, a low-temperature reaction tube 10 is optionally provided after the moisture-absorbing tube 9. The low-temperature reaction tube 10 is made of quartz or ceramics, and it has preferably an inner diameter of 7 to 15 mm and an inner volume of 10 to 60 ml. The low-temperature reaction tube 10 contains a layer 11 of an oxidizing agent and/or a reducing agent, and this tube 10 is heated at about 300° to 700° C. with an electric furnace 12.

According to the method and apparatus of the present invention, a high level of skill is not necessary for the determination of total nitrogen content. Further, the total nitrogen content in samples can be determined by only one analytical operation, irrespective of the form that the nitrogen compounds are present in the samples and even when a high concentration of salts is contained in the sample as in sea water. By the use of a mass fragmentgraphy, the nitrogen content can stably be determined in a high sensitivity without being affected by other components in the reaction system. The method and apparatus of the present invention can be made automatically and very easily, so that the continuous monitoring of the total nitrogen contents in aqueous systems becomes possible.

The present invention will be illustrated with reference to the following examples, which are not however to be interpreted as limiting the invention thereto.

EXAMPLE 1

Total nitrogen content in aqueous urea solutions was determined by using an apparatus as shown in FIG. 1, wherein a quartz tube of 13 mm in inner diameter and 22 cm in length was used as a reaction tube, and as a decomposition catalyst, 6 ml of 20- to 40-mesh alumina beads having 0.1% of palladium deposited thereon were charged in the tube and maintained at 950° C. As a moisture absorber and a carbon dioxide absorber, anhydrous magnesium perchlorate and soda asbestos were used, respectively. As a mass spectrometer, a quadrupole mass spectrometer without a helium separator was used. Helium was used as an inert gas and passed at a rate of 25 ml/minute. Mass fragmentgraph at m/e=28 was measured. Aqueous urea solutions having various concentrations were prepared and 20 μl of each solution was injected into the inlet 4 by means of a microsyringe, and the apparatus was operated, by which a calibration curve was made. A relation between the peak height of the spectrum and the nitrogen concentration in the sample forms a good straight line as shown in FIG. 3. The aqueous urea solutions to be tested were previously freed from dissolved air by passing argon gas through the solution.

EXAMPLE 2

The determination of total nitrogen content was carried out by using an apparatus as shown in FIG. 2, wherein a quartz tube of 13 mm in inner diameter and 22 cm in length was used as a high-temperature reaction tube, and as a decomposition catalyst, 6 ml of 20- to 40-mesh alumina beads having 0.1% of palladium deposited thereon were charged in the tube and maintained at 950° C. Further, a quartz tube of 13 mm in inner diameter and 22 cm in length was used as a low-temperature reaction tube, and 6 ml of copper oxide wire and 10 ml of reduced copper wire, each having a size of 0.1 mmφ×5 mm, were charged in the low-temperature reaction tube as oxidizing agent and reducing agent, respectively, and maintained at 500° C. In each reaction tube, quartz wool was packed below the agent layer and between both the agent layers contained therein. As a moisture absorber and a carbon dioxide absorber, anhydrous magnesium perchlorate and soda asbestos were used, respectively. As a mass spectrometer, a quadrupole mass spectrometer without a helium separator was used. Helium was used as an inert gas and passed at a rate of 25 ml/minute. Mass fragmentgraph at m/e=28 was measured. Aqueous urea solutions having various concentrations were prepared and 20 μl of each solution was injected into the inlet 4 by means of a microsyringe, and the apparatus was operated, by which a calibration curve was made. A relation between the peak height of the spectrum and the nitrogen concentration in the sample forms a good straight line as shown in FIG. 4. In FIG. 4, a line "a" was obtained using the aqueous solution containing dissolved air, and a line "b" was obtained using the aqueous solution from which dissolved air was previously removed by passing argon therethrough.

What is claimed is:

1. An analytical method for the determination of the total nitrogen content in an aqueous system, which comprises:
   (1) introducing a sample aqueous solution together with an inert gas, containing substantially no nitrogen, and carbon monoxide as a carrier gas through a reaction tube, which is packed with a decomposition catalyst, and which is maintained at a temperature of 700° to 1200° C.;
   (2) passing the resulting gaseous mixture through a condenser, thereby condensing and removing water contained in the gaseous mixture;
   (3) passing the gaseous mixture through a moisture-absorbing tube;
   (4) passing the resulting gas through a low temperature reaction tube, which is packed with an oxidizing agent or a reducing agent or both and which is maintained at a temperature of 300° to 700° C.;
   (5) passing the obtained gas mixture through a carbon dioxide-absorbing tube;
   (6) sending the gas mixture coming out of the carbon dioxide-absorbing tube to a mass spectrometer; and
   (7) measuring the nitrogen content of the gas mixture with the mass spectrometer.

2. The method according to claim 1, wherein said inert gas is helium or argon and said decomposition catalyst comprises platinum or palladium.

3. The method according to claim 1, wherein said oxidizing agent is copper oxide or cobalt oxide and said reducing agent is reduced copper or reduced nickel.

4. An analytical apparatus for the determination of the total nitrogen content in an aqueous system comprising:
   a decomposition tube packed with a decomposition catalyst;
   a supply means for introducing an inert carrier gas into the inlet of the decomposition tube;
   an injection means for introducing the sample to be analyzed into the decomposition tube;
   a heating means for maintaining the decomposition tube at a temperature of 700° to 1200° C.;
   a condenser means for condensing and removing water from the gaseous mixture produced in the decomposition tube, said condenser means being disposed downstream from the outlet of the decomposition tube;
   a moisture-absorbing tube packed with a moisture absorber which is disposed downstream from the outlet of the condenser means;
   a lower temperature reaction tube packed with an oxidizing agent and/or a reducing agent, and disposed downstream from the outlet of the moisture-absorbing tube;
   a heating means for maintaining the lower temperature reaction tube at a temperature of 300° to 700° C.;
   a carbon dioxide-absorbing tube packed with a carbon dioxide absorber and disposed downstream from the outlet of the lower temperature reaction tube;
   a mass spectrometer disposed downstream from the outlet of the carbon dioxide-absorbing tube;
   a data processing means for determining the total nitrogen content of the sample from mass spectrographic data derived from the mass spectrometer; and
   conduit means for providing a connection between the decomposition tube, the condenser means, the moisture absorbing tube, the lower temperature reaction tube, the carbon dioxide-absorbing tube and the mass spectrometer.

* * * * *